United States Patent [19]

Feldmann

[11] 4,005,994
[45] Feb. 1, 1977

[54] PROCESS AND APPARATUS FOR CONVERTING SOLID WASTES TO PIPELINE GAS

[75] Inventor: Herman F. Feldmann, Worthington, Ohio

[73] Assignee: Syngas Recycling Corporation, Toronto, Canada

[22] Filed: Dec. 22, 1975

[21] Appl. No.: 643,358

[52] U.S. Cl. .................................. 48/111; 48/209; 201/25; 209/134; 241/DIG. 38
[51] Int. Cl.[2] ........................................ C10J 3/00
[58] Field of Search ............... 48/111, 209, 197 A; 201/2.5, 21, 25; 202/99; 209/11, 134, 135, 136, 137; 241/DIG. 38; 260/676 R

[56] References Cited
UNITED STATES PATENTS

| | | | |
|---|---|---|---|
| 1,773,959 | 8/1930 | Crow | 48/209 |
| 1,837,836 | 12/1931 | Powell | 209/135 |
| 2,595,234 | 5/1952 | Eastman | 48/210 |
| 3,733,187 | 5/1973 | Feldmann | 48/209 |
| 3,817,724 | 6/1974 | Ellis et al. | 48/209 |
| 3,874,116 | 4/1975 | White | 48/209 |

Primary Examiner—Robert L. Lindsay, Jr.
Assistant Examiner—George C. Yeung
Attorney, Agent, or Firm—Sidney W. Millard

[57] ABSTRACT

Solid waste is fed to a confined zone under pressure and contacted with hydrogen containing gas. Partial conversion of the solid waste to methane occurs and the methane containing gas mixture is removed from the confined zone; it is subsequently purified and methanated so as to be a replacement for natural gas. The remainder of the solid waste is discharged from the confined zone as a carbon containing char which is delivered to a separate reaction zone where it is contacted with steam and oxygen under pressure to convert it to synthesis gas (a mixture of hydrogen, water vapor, carbon monoxide and carbon dioxide). The synthesis gas is drawn from the reaction chamber and serves as the hydrogen feed gas into the confined zone. Between the two zones, metal and glass are separated from the char by virtue of their much higher density than the carbonaceous char by entrainment of the char in a jet of steam.

15 Claims, 2 Drawing Figures

PROCESS AND APPARATUS FOR CONVERTING SOLID WASTES TO PIPELINE GAS

BACKGROUND AND SUMMARY OF THE INVENTION

Currently, most cities in the United States are faced with a severe shortage of natural gas that is curtailing industrial operation and expansion, reducing the fuel supplies of institutions such as schools and hospitals and forcing new home construction to utilize expensive electrical energy for heating and cooking which results not only in higher prices but also causes a very low resource utilization efficiency. Because of a continuing decline in the production of natural gas, this crisis will become more severe and even become felt in Canadian metropolitan areas as their growth and energy consumption exceeds the available natural gas supply. In anticipation of this problem, Canada is already reducing exports of natural gas to the U.S. and seriously considering gasification of coal in the western provinces to reduce the impact of the natural gas shortage. Ironically, in the metropolitan areas, where the gas shortages are most severe, the disposal of an ever increasing volume of solid wastes from municipal, industrial and sewage-treatment operations is also a growing problem of major proportions.

Conversion of this solid waste into a synthetic natural gas in an environmentally acceptable fashion would, therefore, assist in the solution of two very severe urban problems. Conversion of solid waste into a fuel gas of much lower Btu than natural gas is possible with known processes and apparatus but production of synthetic natural gas which can be substituted for natural gas has not been commercially practical heretofore. The only process currently available for converting solid wastes into synthetic natural gas is by biological digestion. The two main problems with biological digestion are:

1. The long solid waste residence time requiring extremely large vessel capacity if large volumes of waste are to be treated.
2. Disposal of the by-product sludge from the process.

The invention described here offers the following advantages over prior processes:

1. No preseparation of metal and glass is required.
2. Higher yields of methane are produced than are possible by alternate technology.
3. Gas is produced at the proper pressure for purification.
4. The recycle value of the metal and glass is preserved because no oxidation or sintering occurs.
5. Relatively small volume of disposable residue.

General background to the technology is given in U.S. Pat. Nos. 3,733,187 and 3,729,298. For the purpose of this invention, the two patents are incorporated by reference as background information and showing the state of the art.

It is the intention of this disclosure to teach how to take solid wastes from municipal garbage and trash disposal systems, sewage treatment systems, industrial waste collection, etc. and convert the same into usable hydrocarbons on a practical basis with a minimum of ash to be disposed of at the end of the process. This invention also teaches how to greatly increase the yield of methane per unit of waste over that achieved using prior-art conversion systems.

While there are a wide variety of possible individual chemical constituents in the infinite variety of solid waste materials enumerated, the fact is that as a total group comingled in the ordinary course of transportation to a fill site or treatment plant, the distinction in quantities of chemical composition is somewhat limited. For the most part, the solid waste includes large portions of carbon and considerable oxygen and hydrogen. It is a prime objective of this invention to convert the carbon to usable gaseous hydrocarbons.

It is well known that contacting solid waste with hydrogen containing gas will convert certain of the carbon compounds to methane, ethane, and perhaps other hydrocarbons. This invention illustrates:

1. That it is advantageous to physically separate the methane production reactor from the gasifier reactor in which the hydrogen containing synthesis gas is produced. The methane production reactor being a confined zone under pressure where solid waste is contacted with hydrogen containing gas. The gasifier reactor being a chamber under pressure where carbonaceous residue (called char) from the confined zone is contacted with steam and gaseous oxygen.

2. That it is desirable to control the degree of carbon conversion in the methane production reactor below a critical level to insure that sufficient carbonaceous char is delivered to the gasifier reactor. With proper quantities of char delivered to the gasifier reactor the synthesis gas produced therein will have enough sensible heat to bring the solid wastes to reaction temperature (when the synthesis gas is delivered to the methane production reactor).

3. There is a point of steady state operation within the system at given solids, steam and oxygen feed rates, system pressure, and types of methane production reactors and gasification reactors where almost all carbon in the waste is consumed or converted during the process.

4. The point of steady state operation shifts upon modification of one or more of the variables enumerated above to another steady state point.

5. The yield of methane and consumption of oxygen per unit of solid waste treated depend on this steady-state operation point. In general, the closer operation in the methane production reactor is to maximum carbon conversion levels, the higher will be the methane yield and the lower the oxygen consumption.

It is believed that carbon compounds in solid waste become subject to cracking in the confined zone under pressure and temperature, and that with hydrogen gas available, the cracking carbon molecules tend to react with the hydrogen to form methane. Whereas, in the absence of hydrogen, the tendency is to polymerize and form longer carbon chains with an increase in the formation of hydrocarbon gum and tar. It has been experimentally determined that a pressure of about 18 atmospheres is satisfactory to achieve the degree of conversion desired and to produce a gas that is both rich in methane and low in tars. At this pressure, reactor vessels may be economically constructed and the cost of the subsequent purification of the product gas from the methane production reactor is much reduced over what it would be at atmospheric pressure. In addition, the feeding of the solid wastes into the confined zone by the use of conventional lock hoppers can be accomplished at this pressure. Therefore, the major portion of the experimental work upon which this concept is based was carried out close to 18 atmospheres pressure.

Given this parameter, the temperature of the reaction chamber becomes important because at too high a temperature the methane produced tends to be cracked into carbon and hydrogen. It was discovered that a satisfactorily high yield of methane can be achieved in the methane production reactor at bulk temperatures of 900° C although the hydrogen containing gas mixture can be fed into the confined reaction zone at much higher temperatures because thermal equilibrium will be reached very rapidly between the cooler waste and the hot hydrogen containing gas. The carbon of the solid waste is partially converted to methane and small quantities of other low molecular weight hydrocarbons in the confined zone and the gaseous mixture is drawn off to a cleaning and purifying zone where carbon dioxide is removed and additional methane is formed by the reaction of the excess carbon monoxide and hydrogen in the product gas. After this treatment the resulting gas can be used as a replacement for natural gas.

Carbon containing char is discharged from the confined zone after the partial conversion to fall through a generally vertical duct toward a quenching bath of water. A side branch off the vertical duct is arranged to receive a transversely directed jet of steam which will carry along with it the lighter weight solid waste (mostly char) while the heavier solid waste (usually glass and metal) will fall on downward toward the quenching water bath where the heat contained in the metal and glass will be recovered by conversion to steam which drifts upward countercurrent to the falling glass and metal.

The char blown into the side branch by the jet of steam is directed to a reaction chamber and oxygen is injected simultaneously into the chamber. The combination of carbon containing char, steam and oxygen at a pressure of approximately 18 atmospheres causes well known gasification chemical reactions to occur with the resulting formation of synthesis gas consisting essentially of carbon monoxide, carbon dioxide, hydrogen gas and some leftover water vapor. Overall, the gasification reactions are exothermic but require a temperature above 900° C for reaction to occur at a commercially reasonable rate. The heat is supplied by combustion of part of the carbon with oxygen. Hot synthesis gas is withdrawn from the gasifier and delivered to the methane production reactor to provide the hydrogen containing gas used for the methane forming reactions. The ash residue remaining in the reaction chamber following the gasification is only a very small percentage of the net weight of the solid waste initially delivered to the confined zone.

DESCRIPTION OF THE PREFERRED EMBODIMENTS

Figure 1:
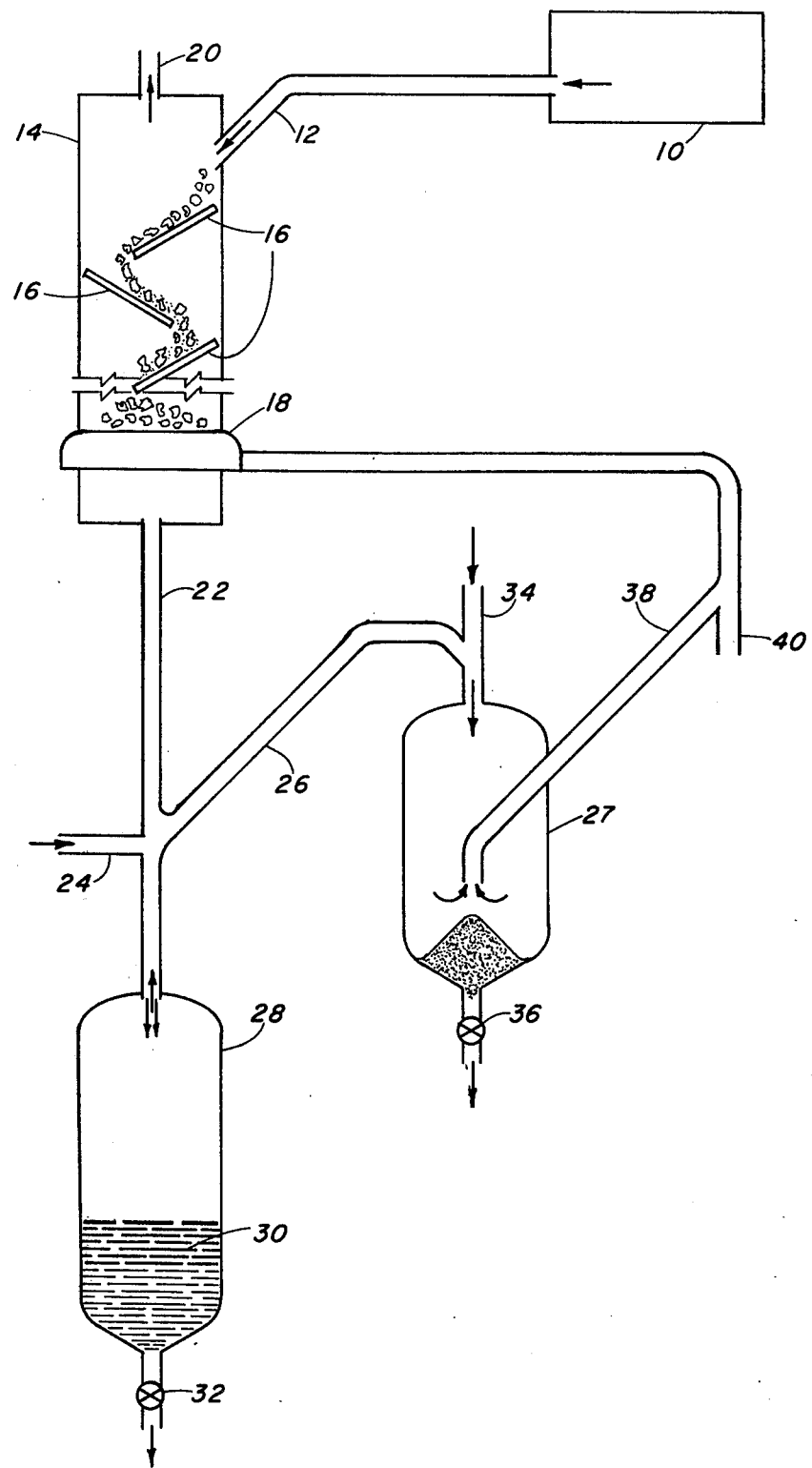
FIG. 1 is a diagrammatic view of the basic elements of the apparatus necessary for this invention.

Initially in the operation of this invention the solid waste to be utilized is comminuted by a conventional trash shredder 10. It is then delivered by suitable feed hoppers, seals, and metering mechanism (not shown) through duct 12 to a confined zone or methane production reactor 14.

As illustrated, the confined zone 14 has baffle means 16 projecting radially inward from its sides to retard the flow of solid waste through the chamber. This invention embodies the freefall concept with any baffling necessary as well as a moving-bed type of structure and the illustration of bafflers 16 is merely one example of means for retarding the passage of solid waste. Such feed screws and agitating means as would be inherent in a moving-bed type of operation are within the inventive concept. The required residence time of the solid waste in the confined zone 14 is a function of type of reactor, particle size, pressure and temperature as will be explained subsequently.

Synthesis gas is fed by a distributor 18 into the lower section of the confined zone 14 and it moves upward, counter-current to the flow of the solid waste. Chemical reactions take place in the confined zone, as will be explained subsequently, and the resulting reaction gases are drawn off near the top of zone 14 at 20. The gases drawn off through the outlet 20 are delivered elsewhere for cooling and purification. Such purification may consist of methanation, removal of acid gases such as $CO_2$ and $H_2S$ and whatever else is necessary to produce a clean burning hydrocarbon gas. The purification process to get the desired hydrocarbon mixture forms no part of this invention and such apparatus and techniques are well known to those having ordinary skill in the art and will not be described.

The unreacted solid waste continues on through the vertical confined zone and out through appropriate valving to a generally vertical duct 22 where the solid waste is in free fall condition. This vertical, free fall duct 22 will be employed whether the confined zone 14 is of the moving bed or free fall design.

It is anticipated that the comminuted or shredded solid waste from the shredder 10 will contain metal, glass, paper, bone and all sorts of other solid materials and it is necessary to separate the carbon containing portions of the unreacted solid waste (called char) from the noncarbon containing materials. Accordingly, a high pressure jet 24 is provided along one side of the free fall duct 22 and a jet of steam is directed transversely across the path of free falling solid waste. Immediately across the duct from jet 24 is a side branch 26 which leads to a second reaction chamber 27. Because of the velocity of the steam from jet 24 and the location of the side branch 26, the lighter weight carbon containing solid waste will be deflected into branch 26 and thereby separated from the heavier, free falling metal and glass. The heavier particles will fall past the side branch 26 downward into a heat extraction chamber 28 containing a water bath 30. The heat of the metal and glass will be extracted by the water; saturated steam from bath 30 will drift or be forced upward toward duct 22, countercurrent to the falling glass and metal, and will be drawn or driven by the jet 24 into the side branch 26.

Valving 32 is indicated at the bottom of the heat extraction chamber for the purpose of allowing the discharge of metal and glass from the bath as a water slurry.

Turning back to the second reaction chamber 27, a charge of oxygen is injected into the moving stream of steam and char at 34 as it enters the chamber. The carbon in the char reacts with the steam and oxygen to form a synthesis gas. The exact composition of this synthesis gas will depend on how the gasifier is operated. There are several species of gasification systems which are technically possible. The type of contacting scheme is optional and may include a moving bed, a fluidized bed and/or entrained gasification. For this particular application, an entrained gasifier is preferred because it is simpliest to integrate with the methane production reactor and, therefore for illustrational purposes, the following calculations are based on results reported for an entrained gasifier. A typical synthesis gas from an entrained gasifier would include the following major compounds in approximately the shown proportions.

| Name | Percentage |
|---|---|
| Carbon monoxide | 35 |
| Hydrogen | 35 |
| Carbon dioxide | 10 |
| Water Vapor | 20 |

At gasification temperatures (above 900° C), all of the oxygen is consumed and substantially all of the carbon in the char will be converted to the gaseous products listed above with anything not converted being discharged as ash through valving 36. The combination of the oxygen and steam with the char is an exothermic reaction which is designed in this operation to raise the temperature of the synthesis gas formed in reaction chamber 27 to about 1245° C and it is drawn off through ducting 38 to be delivered at about that temperature to the distributor 18 at the lower portion of the confined zone 14.

There are several interrelated parameters which determine the conditions which result in acceptable operation. Specifically, there are six design or operating parameters which can be controlled and which will influence the operation of the system. They are as follows:
 1. Type of methane production reactor
 2. Residence time of waste in methane production reactor
 3. Type of gasification reactor
 4. Residence time of char in gasification reactor
 5. Feed rates for steam and oxygen to gasification reactor
 6. System pressure The parameters are described in more detail below.

1. The Type of Methane Production Reactor

Two contacting schemes, free-fall and moving-bed, have been experimentally evaluated and results are shown in the examples section. Both moving-bed and free-fall contacting schemes allow the most efficient utilization of the heat contained in the hot gases passing up through the reactor by allowing the heat contained in the gas to dry and preheat the solids. The confined zone 14 may be thought of as three zones stacked one on top of the other. When the waste is fed to the confined zone it must be (1) dried, (2), heated and (3) reacted. Thus, for thermal efficiency the synthesis gas is forced counter current to waste flow. Hot synthesis gas is delivered to the methane production reactor by the distributor 18 (at about 1260° C.) and it reacts with the heated and dried solid waste to form methane. The gases formed move upward in a cooler state and heat the downwardly moving waste to reaction temperature. Continuing on upward the even cooler gases dry the incoming wet waste before being drawn off through port 20. Thus, the heat from the synthesis gas is used in three stages to extract as much heat as can be economically useful.

The exit temperature of the gas for these two alternative contacting schemes is much lower than for fluid-bed operation where the gas exits at the reaction temperature. It is preferable to have the gas exit the methane production reactor at as low a temperature as is possible because effective heat recovery from the hot gas outside the reactor is difficult as the dirty nature of the gas causes heat exchanger fouling problems.

In addition, moving-bed or free-fall operation will allow operation with a wider range moisture contents of solid wastes without requiring predrying of the waste or modification of other operating parameters. Another advantage of the two schemes experimentally evaluated is that the waste conversion temperatures will remain relatively constant with varying moisture content of the solid wastes whereas in a fluid bed the temperature will be affected by variations in waste moisture content. Changes in the moisture content of the solid waste in the free-fall and moving-bed systems simply changes the exit temperature of the product gas rather than changing the reaction temperature as it would in a fluid bed.

2. The Solid-Waste Residence Time in the Methane Production Reactor

Solid-waste residence time studies have varied from approximately one second in the free-fall experiments up to approximately one half hour in the moving-bed experiments with successful operations being conducted between the extremes. Briefly, the conclusion of this study is that a substantial amount of methane is formed at a rate that is limited only by the heat transfer rate to the particle. For example, the methane yield at a one-second residence time typical of free-fall operation is approximately 80 percent of that for a moving-bed run where the waste residence time is on the order of 15 minutes. Therefore, the rather broad range of residence times ranging from 1 second for a free-fall reactor system to 30 minutes for a moving-bed system will allow sufficient conversion of the solid waste. It should also be pointed out that if conversion levels in the methane production reactor are too high, then the carbon content of the char will be too low to properly fuel the gasification reactor, as will be explained subsequently.

3. The Type of Gasification Reactor

Here, as in the case of the methane production reactor, one can select from contacting options including moving-bed, fluid-bed, free-fall counter current, or cocurrent entrained reactor systems to convert the carbonaceous char from the methane production reactor to synthesis gas. Because of the low-bulk density of the carbonaceous char which ranges from about 5 to 15 lbs/ft$^3$ (0.08 to 0.24 gms/cm$^3$), a cocurrent entrained system seems particularly attractive for the gasification reactor because of its mechanical reliability and ability to completely utilize the carbon remaining in the carbonaceous char.

With this selection, a projected waste feed rate and a selected system pressure, the feed rates of steam and oxygen can be calculated to achieve the desired proportions of gases in the synthesis gas. With the calculated values being injected the system will quickly reach equilibrium as will be explained subsequently.

4. The Residence Time of Char in the Gasification Reactor

The residence time required to convert the carbonaceous char completely to synthesis gas depends heavily on the temperature in the gasification reactor. Since, for the reasons outlined above, we favor the use of an entrained reactor, char residence time will be on the order of seconds. Thus, relatively high temperatures are required. These higher temperatures are also required to provide sufficient heat to the methane production reactor as explained above.

For example, 2300° F (1260° C) synthesis gas would allow both the complete conversion of carbon in the char in the gasification reactor as well as providing enough heat to carry out the conversion of the solid waste in the methane production reactor, assuming the raw waste contains up to 20 percent moisture. At this temperature almost complete carbon conversion could be achieved in the second or so residence time typical of the preferred entrained gasification reactor.

5. Steam and Oxygen Feed Rates

The steam and oxygen feed rates provides the key control of gasifier temperature which, as pointed out above, is the key parameter in providing heat for the methane production reactor and insures complete carbon utilization in the gasifier reactor.

Since the influence of steam and oxygen rates on carbon gasification temperatures have been reported (in Chemistry of Coal Utilization, published by John Wiley in 1963, particularly at pages 988 to 992) and are calculable (unlike the processes occuring in the methane production reactor) the details of these calculations will not be repeated here.

Temperature ranges for the synthesis gas that appear to be most practical for the integrated system vary from 1900° F (1038° C) to about 2500° F (1370° C) and the oxygen-feed rate would be adjusted to provide the proper temperature. (The temperature can be raised by injecting more oxygen which will increase the proportion of $CO_2$ in the synthesis gas.) The lower end of the synthesis gas temperature range is determined by the need to achieve high carbon conversion levels in the gasification reactor and the upper temperature level is dictated by the moisture content of the solid waste fed to the methane production reactor.

6. The System Pressure

The optimum pressure is one that will allow a reasonable balance between the following factors.
 a. The ability to feed solids from atmospheric pressure into a pressurized vessel.
 b. The investment cost in the plant reactor vessels.
 c. The cost of gas purification.
 d. The ability to produce methane and minimize the production of tars.

Because of the lack of data on the effect of pressure on the types of products to be formed in the methane production reactor the pressure for the experimental studies was selected on the basis of (a) the ability to feed solids, (b) the cost of gas purification, and (c) to a lesser extent, the estimate of what vessel costs would be. Based on these considerations 250 psig (18 atm) was selected to be the pressure at which to conduct experimental studies. As the data in the attached example indicate, 250 psig (18 atm) allowed high methane yields and provided surprisingly low tar yields. At lower pressures gas purification costs increase very rapidly and at higher pressures the difficulty of feeding solids into pressure vessels increases.

OPERATION OF THE INTEGRATED METHANE PRODUCTION REACTOR AND GASIFICATION REACTOR

The mechanical operation of the reactor system and the factors influencing the selection of design and operating parameters have been described above. Next, experimental data generated for the methane production reactor and calculated results for an entrained gasification reactor are used to demonstrate how the two reactor systems reach an equilibrium balance such that all the carbon fed in with the solid waste is utilized to produce either methane or ethane directly or carbon monoxide and hydrogen which can be used to produce additional methane by the well known methanation reaction ($CO + 3H_2 \rightarrow CH_4 + H_2O$).

For example, it has been found experimentally that the carbon converted to methane in the methane production reactor increases with increasing hydrogen in the feed gas to the methane production reactor. At the same time the volume of synthesis gas generated depends on the quantity of carbon in the char fed to the gasifier. Increased carbon results in an increased synthesis gas and thereby increased hydrogen volume.

Figure 2:
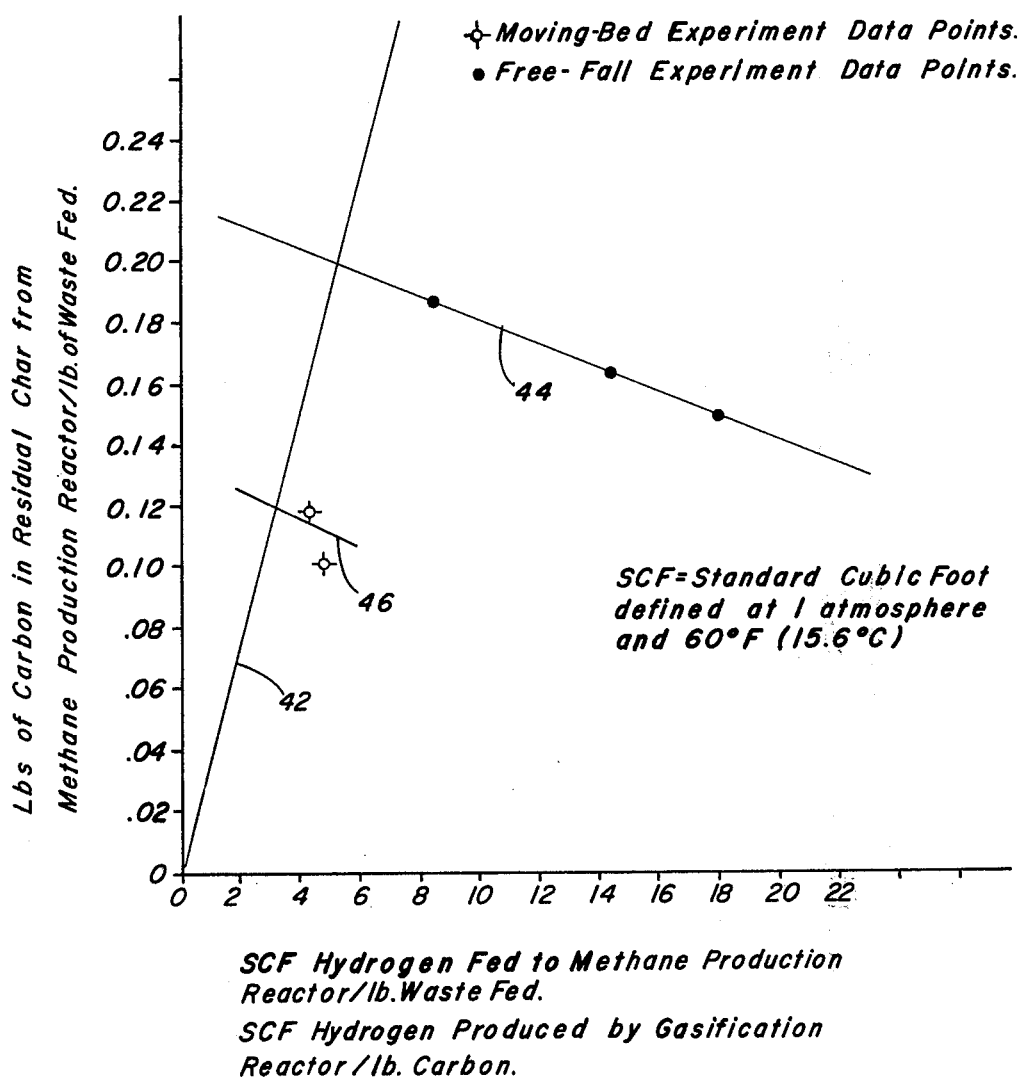
FIG. 2 is a graph of experimental and calculated values useful in the invention.

Observing FIG. 2, curve 42 shows the hydrogen in the synthesis gas from an entrained gasifier as a function of the carbon fed to the gasifier and was calculated using the aforementioned correlations in the treatise "Chemistry of Coal Gasification". Curves 44 and 46 are plotted from experimental data reported in the example which follows.

Two parallel trends (curves 44 and 46) are shown in FIG. 2 where the experimental data showing how the carbon in the residual char from the methane production reactor depends on the hydrogen fed to the methane production reactor is plotted for both free-fall (curve 44) and moving-bed (curve 46) experiments in the methane production reactor. In addition, FIG. 2 shows how the quantity of hydrogen in the synthesis gas increases with the carbon that is available for its production. Thus, the intersection of curve 42 with the curve 44 or curve 46 is where the system will operate at equilibrium i.e., where the carbon in the char will provide sufficient hydrogen to achieve that particular carbon conversion. This balance point is a very stable one and changes in conditions that can occur with fluctuations in system parameters will be automatically compensated for.

For example, assume there is too much carbon in the char to satisfy the hydrogen/solid waste feed ratio to the confined zone 14. This automatically causes an increase in hydrogen generated in the gasification reactor. This increased hydrogen is fed to the methane production reactor which increases the carbon conversion to methane which would obey the experimental relationship shown in FIG. 2 and carbon conversion to methane would increase until the equilibrium point is reached, that is, the point of intersection of the two curves as shown in FIG. 2. The curve 46 for moving-bed operation falls below that for free-fall operation, curve 44, because the carbon conversion to gas would be higher at any hydrogen/water-feed ratio thereby leaving less carbon in the char for synthesis gas production.

One critical factor which is maintained is a temperature which is not high enough to melt and fuse together the glass and metal portions of the solid which could clog the passage of the solids from the heat-recovery chamber 28. When the reactor operates in the free-fall mode melting will probably not be a problem because the short residence time of the particles will not allow them to become fluid. However, in moving-bed operation the temperature of the synthesis gas entering the methane production reactor should be maintained below that which will melt and fuse together the metal and glass portion of the solid wastes. The synthesis gas temperature is probably best controlled by the injection of additional steam into the synthesis gas transfer line 38 as at 40.

As indicated previously, the feed rates of the waste, oxygen and steam are variable but once desired parameters are established, the feed rates will be constant. Unfortunately, the self regulating factors illustrated by FIG. 2 are limited in their application with fixed feed rates. For example, if the waste fed to the confined zone becomes carbon rich due to some specialized refuse discharge the resulting char will also be carbon rich. The natural factors will tend to drive the system to a different equilibrium point along line 42. However, if the degree of carbon change in the char is too great the system will operate at steady state at a point off line 42 which is less than optimum conditions.

However, this condition can be detected by a sampling of the synthesis gas in duct 38 and a measuring of the carbon monoxide-carbon dioxide ratio. If the ratio is different than about three and one half to one then the oxygen and steam rates should be modified to restore the maximum efficiency desirable.

EXAMPLE

Some typical experiments conducted in a methane production reactor pilot plant are shown in Table 1. The pilot plant utilized for these experiments was a 3-inch (7.6 cm) I.D. vessel with provision for the constant feeding of solid waste (shredded to about one centimeter on a side) and withdrawal of the resulting carbonaceous char. The system was designed to operate at temperatures of about 900° C at a pressure up to 100 atmospheres. But as these results indicate a pressure of 18 atmospheres proved to be adequate to produce a gas that after purification and methanation would be substitutable for natural gas and at the same time produce minimal liquid products.

Other experiments were made that verify the results shown here. Full details for these runs are not tabulated here however because they were of shorter duration.

The solid waste used in these experiments was of a standard composition recommended by the Environmental Protection Agency for incineration studies that was modified somewhat to allow passage through the 7.6 cm methane production reactor without bridging. Typically, the solid waste used in these experiments had the following elemental balance.

Composition of Standard Solid Waste Used

| Constituent | Weight Percent |
|---|---|
| Carbon | 35.2 |
| Hydrogen | 4.9 |
| Nitrogen | 0.2 |
| Oxygen | 35.5 |
| Ash | 1.3 |

-continued

Composition of Standard Solid Waste Used

| Constituent | Weight Percent |
|---|---|
| Moisture | 22.9 |
| | 100.0 |

TABLE 1

SUMMARY OF TYPICAL METHANE PRODUCTION REACTOR PILOT PLANT OPERATION
Free-Fall Experiment - Run No. 6

Solid Waste Feed Rate = 11.8 lbs/hr (5.36 kg/hr)
Hydrogen Feed Rate = 98 std cu ft/hr
Pressure = 250 psig (18 atm)
Reactor Temperature = 1600° F (871° C)
Approximate Solid Waste Residence Time = 1 second
Carbonaceous Char Yield = 0.271 lbs/lb-waste as fed
Oil Yield = not measured (less than 1%)
Water Yield = 0.220 lbs/lb-waste as fed
Product Gas Yield = 14.5 std cu ft/lb-waste as fed
(18.5 std cu ft/lb-dry waste)

Product Gas Composition (Volume percent, dry basis)

| | | |
|---|---|---|
| $H_2$ | = | 61.1 |
| $CH_4$ | = | 12.9 |
| $CO$ | = | 17.4 |
| $CO_2$ | = | 4.6 |
| $C_2H_6$ | = | 1.5 |
| $C_2H_4$ | = | 0.1 |
| $C_6H_6$ | = | 0.6 |
| $N_2$ | = | 1.8 |
| | | 100.0 |

Moving-Bed Experiment - Run No. 10

Solid Waste Feed Rate = 10.8 lbs/hr (4.90 kg/hr)
Hydrogen Feed Rate = 50.0 std cu ft/hr
Pressure = 250 psig (18 atm)
Temperature = 1600° F (871° C)
Approximate Solid Waste Residence Time = 21 minutes
Carbonaceous Char Yield = 0.154 lbs/lb waste as fed
Oil Yield = 0.008 lbs/lb waste as fed
Water Yield = 0.248 lbs/lb waste as fed (from moisture in solid waste)
Product Gas Yield = 8.7 std cu ft/lb waste as fed
(11.6 std cu ft/lb-dry waste)

Product Gas Composition (Volume percent, dry basis)

| | | |
|---|---|---|
| $H_2$ | = | 32.42 |
| $CH_4$ | = | 27.34 |
| $CO$ | = | 24.20 |
| $CO_2$ | = | 13.30 |
| $C_2H_6$ | = | 1.50 |
| $C_6H_6$ | = | 0.50 |
| $N_2$ | = | 0.74 |
| | | 100.00 |

Moving-Bed Experiment - Run No. 11

Solid Waste Feed Rate = 10.4 lbs/hr (4.72 kg/hr)
Hydrogen Feed Rate = 44.2 std cu ft/hr
Pressure = 250 psig (18 atm)
Temperature = 1500° F (816° C)
Approximate Solid Waste Residence Time = 13 minutes
Carbonaceous Char Yield = 0.173 lbs/lb-waste as fed
Oil Yield = 0.008 lbs/lb-waste as fed
Water Yield = .337 lbs/lb-waste as fed
Product Gas Yield = 7.0 std cu ft/lb-waste as fed
(10.6 std cu ft/lb-dry waste)

Product Gas Composition (Volume percent, dry basis)

| | | |
|---|---|---|
| $H_2$ | = | 33.8 |
| $CH_4$ | = | 23.8 |
| $CO$ | = | 24.7 |
| $CO_2$ | = | 13.2 |
| $C_2H_6$ | = | 1.9 |
| $C_2H_4$ | = | 1.3 |
| $C_3H_8$ | = | 0.2 |
| $C_6H_6$ | = | 0.7 |
| $N_2$ | = | 0.4 |
| | | 100.0 |

The raw gas shown above must be purified and methanated before it is substitutable for natural gas. In all cases, this is possible using available technology and the heating value of the final product gas will range from 950 plus to over 1000 Btu/std cu ft making it substitutable for natural gas in all applications.

Having thus described the invention in its preferred embodiment obvious modifications of parameters will be clear to those having ordinary skill in the art. Accordingly, it is not the intention of the inventors to be limited except by the wording of the appended claims.

I claim:

1. Apparatus for converting solid waste to methane-containing gas comprising:

a methane-containing gas production reactor including means for delivering solid wastes of given moisture content to input duct means of an elongate confined zone of said methane-containing gas production reactor, said elongate zone and said duct means being configured and arranged to effect movement of said wastes along said zone, said zone being under pressure;

means for introducing synthesis gas exhibiting a given thermal energy to said zone at a location remote from said input duct means, said synthesis gas including a mixture of carbon monoxide, carbon dioxide, hydrogen, and water vapor;

said zone being configured and arranged with respect to said delivery of said wastes and said synthesis gas to control the rate of passage of the wastes through the zone, said means introducing said synthesis gas being situated to effect movement of said gas along said zone in a direction countercurrent to and confronting said moving wastes, whereby, as said wastes move through said zone there is a progressive diminution of said moisture in said wastes, said synthesis gas and said wastes being in contact and under sufficient temperature and pressure to partially convert the wastes into methane-containing gas, and there is produced a carbon containing char;

means for removing the methane-containing gas from the zone;

means for effecting the withdrawal of the char from the zone;

a gasification reactor and means for delivering oxygen and water vapor and said char, in a condition substantially free of inorganic components of said wastes, to said reactor under sufficient pressure and temperature to convert a part of said char, oxygen and water vapor to said synthesis gas, said gasification reactor comprising the source of synthesis gas delivered to said zone; and means for delivering the synthesis gas from the gasification reactor to said introducing means.

2. The apparatus of claim 1 including a stirring system to control a moving bed of said solid waste in its rate of passage through said zone.

3. The apparatus of claim 1 including means for separating the char from metal, glass and the like after it leaves said zone.

4. The apparatus of claim 3 including means for extracting heat from the separated metal, glass and the like by delivering it to a water bath.

5. The apparatus of claim 3 wherein the means for separating char from metal, glass and the like comprises a vertically extending duct with a side branch, means forming a jet of water vapor into said duct transverse to the movement of solid material in said duct for forcing the ligher weight solid materials including the char into the side branch but allowing the heavier weight metal, glass and the like materials to fall past the side branch.

6. The apparatus of claim 1 wherein the zone comprises a vertically extending conduit allowing said solid waste to fall from the top to the bottom of said conduit and wherein said conduit is configured to include means for retarding the free fall of the waste.

7. The apparatus of claim 6 wherein the retarding means comprises baffle means extending from the walls of the zone transverse to the direction of fall of the waste.

8. The apparatus of claim 6 including means for separating the char from metal, glass and the like after it leaves the zone.

9. The apparatus of claim 8 including means for extracting heat from the separated metal, glass and the like by delivering it to a water bath.

10. The apparatus of claim 6 wherein the means for separating char from metal, glass and the like comprises a vertically extending duct with a side branch, means forming a jet of water vapor into said duct transverse to the movement of solid material in said duct for forcing the lighter weight solid materials including the char into the side branch but allowing the heavier weight metal, glass and the like materials to fall past the side branch.

11. A process for converting solid waste of given moisture content to methane-containing gas comprising:

delivering said waste under pressure to an input of a confined zone, said zone being configured for movement of said waste therealong from said input;

contacting the waste during said movement thereof, in countercurrent fashion, with hydrogen-carrying synthesis gas exhibiting given thermal energy sufficient to heat said waste and progressively effect, as said waste moves from said input, a diminution of said moisture content, a formation of methane-containing gas, and a formation of carbon containing char;

removing said methane-containing gas from said zone, said methane-containing gas comprising a mixture of hydrocarbons, water vapor, hydrogen, carbon dioxide and carbon monoxide;

removing the remaining solid waste from the confined zone, delivering the carbon containing char, in a condition substantially free of inorganic components of said waste, to a gasification reactor and reacting it with oxygen and water vapor to form said hydrogen-carrying synthesis gas, said synthesis gas including carbon monoxide, carbon dioxide, hydrogen, and water vapor; and delivering the synthesis gas to the confined zone for effecting said countercurrent contact thereof with said wastes.

12. The process of claim 11 wherein the char is separated from glass, metal and the like before it is delivered to the gasification reactor by providing a jet of gaseous material directed transverse to vertically falling solid waste discharged from the confined zone, the lighter weight char being deflected by the jet into the gasification reactor.

13. The process of claim 12 wherein the jet of gaseous material is water vapor.

14. The process of claim 12 including recovering heat from the separated glass, metal and the like by delivering it to a water bath.

15. The process of claim 11 including removing all unreacted solids from said gasification reactor with said solids being substantially free of carbon, substantially all said carbon having been converted to gaseous products in said confined zone and said gasification reactor.

* * * * *